United States Patent
Alden et al.

(10) Patent No.: US 10,456,289 B2
(45) Date of Patent: Oct. 29, 2019

(54) METHOD AND DEVICE FOR THE MANAGEMENT OF BODY FLUIDS LEAKING FROM A SURGICAL DRAIN TUBE INCISION

(71) Applicants: Dmitri Alden, New York, NY (US); Paul Mulhauser, New York, NY (US)

(72) Inventors: Dmitri Alden, New York, NY (US); Paul Mulhauser, New York, NY (US)

(73) Assignee: ALDEN ADVANCED TECHNOLOGIES, INC., Jacksonville, FL (US)

( * ) Notice: Subject to any disclaimer, the term of this patent is extended or adjusted under 35 U.S.C. 154(b) by 0 days.

(21) Appl. No.: 16/272,271

(22) Filed: Feb. 11, 2019

(65) Prior Publication Data

US 2019/0254863 A1    Aug. 22, 2019

Related U.S. Application Data

(63) Continuation-in-part of application No. 15/901,166, filed on Feb. 21, 2018, now Pat. No. 10,238,528.

(51) Int. Cl.
*A61F 5/443* (2006.01)
*A61F 5/44* (2006.01)
(Continued)

(52) U.S. Cl.
CPC ............ *A61F 5/443* (2013.01); *A61F 5/4405* (2013.01); *A61M 25/02* (2013.01); *A61M 27/00* (2013.01); *A61M 2025/0246* (2013.01)

(58) Field of Classification Search
CPC ................... A61F 5/448; A61F 5/4405; A61F 2013/00089; A61F 5/4407; A61F 5/441;
(Continued)

(56) References Cited

U.S. PATENT DOCUMENTS 2,902,036 A  *  9/1959  Murle .................... A61F 5/442
                                                                    604/334
3,780,739 A     12/1973  Frank
(Continued)

OTHER PUBLICATIONS

International Search Report and Written Opinion, issued by the I.S.A./ U.S. Receiving Office, regarding corresponding international patent application Serial No. PCT/US2018/018928, dated May 2, 2018; 8 pages.
(Continued)

*Primary Examiner* — Tatyana Zalukaeva
*Assistant Examiner* — Gabriella E Burnette
(74) *Attorney, Agent, or Firm* — Fox Rothschild LLP

(57) ABSTRACT

A fluid collection system is provided. The fluid collection system broadly includes a baseplate having an adhesive backing configured to couple the baseplate to a patient's skin and defining a wafer having an approximately centrally positioned opening that receives a first end of a surgical drain tube, and a wafer connector disposed around said opening. An appliance includes a leaked fluid remover that includes a fluid remover connector operable to detachably couple with the wafer connector. The leaked fluid remover includes an outer septum and an inner septum for receiving the surgical drain tube. The outer septum is capable of moving about radially, axially and/or pivotally to alleviate side load tension on the septum caused by displacement of the surgical drain tube.

17 Claims, 15 Drawing Sheets

(51) Int. Cl.
*A61M 25/02* (2006.01)
*A61M 27/00* (2006.01)

(58) Field of Classification Search
CPC ....... A61F 5/443; A61M 27/00; A61M 39/12; A61M 31/00; A61M 39/06; A61M 1/008; A61M 1/0088; A61M 1/0021; A61M 5/178; A61M 25/0014; A61L 24/00; A61L 28/00; A61J 15/0053
USPC ........................................................ 604/319
See application file for complete search history.

(56) References Cited

U.S. PATENT DOCUMENTS

| | | | | |
|---|---|---|---|---|
| 4,050,461 | A | * | 9/1977 | Ruby ..................... A61F 5/442 604/277 |
| 4,846,820 | A | | 7/1989 | Jensen |
| 4,941,869 | A | | 7/1990 | D'Amico |
| 5,236,426 | A | | 8/1993 | Schottes et al. |
| 5,503,625 | A | | 4/1996 | Plass |
| 5,628,732 | A | * | 5/1997 | Antoon, Jr. ......... A61B 17/3462 604/167.06 |
| 5,738,661 | A | * | 4/1998 | Larice .................... A61F 5/442 604/180 |
| 5,752,938 | A | | 5/1998 | Flatland et al. |
| 5,935,115 | A | * | 8/1999 | Espina ................... A61F 5/445 604/276 |
| 9,707,120 | B2 | * | 7/2017 | Nguyen-DeMary ........................ A61F 5/4407 |
| 2005/0171490 | A1 | | 8/2005 | Weaver et al. |
| 2007/0282271 | A1 | | 12/2007 | Kaplan et al. |
| 2008/0177252 | A1 | | 7/2008 | Isik |
| 2014/0213995 | A1 | * | 7/2014 | Garrettson ............. A61F 5/448 604/344 |

OTHER PUBLICATIONS

International Search Report and Written Opinion, issued by the I.S.A./ U.S. Receiving Office, regarding corresponding international patent application Serial No. PCT/US2019/017491, dated Apr. 23, 2019; 9 pages.

* cited by examiner

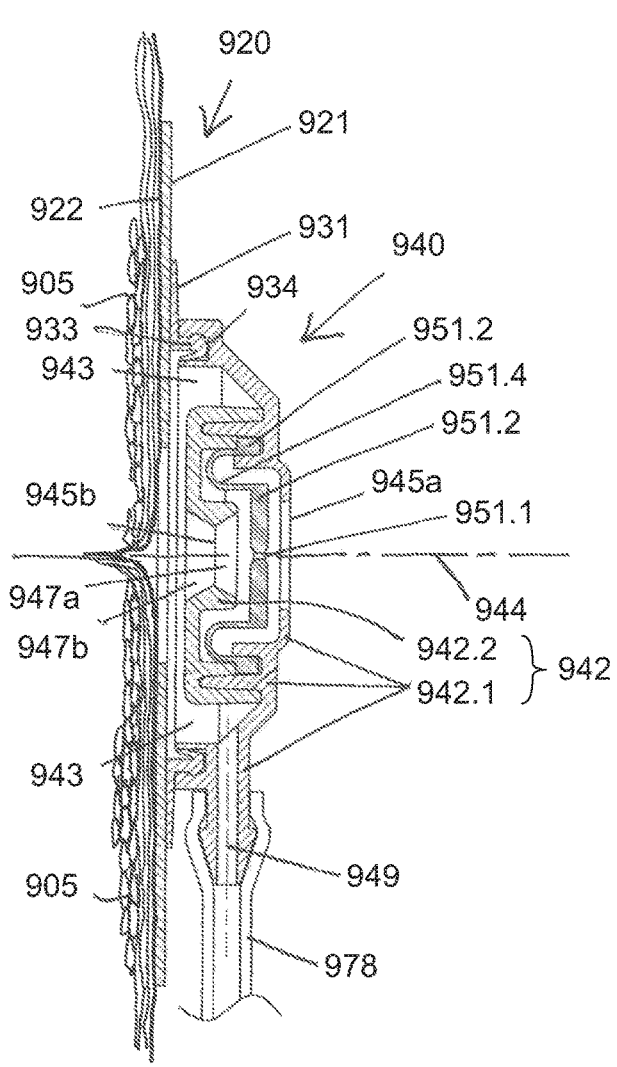
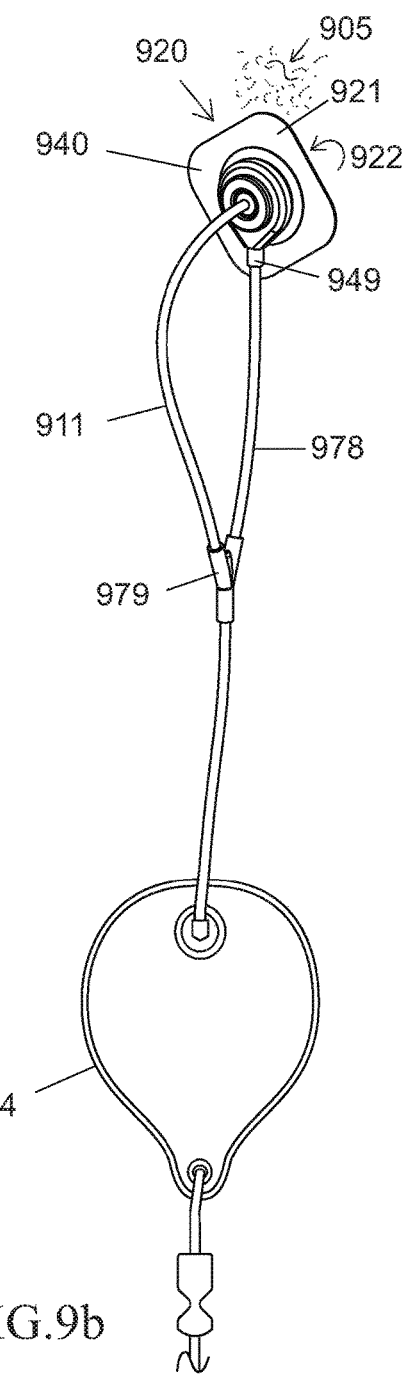
FIG.9a
FIG.9b

US 10,456,289 B2

METHOD AND DEVICE FOR THE MANAGEMENT OF BODY FLUIDS LEAKING FROM A SURGICAL DRAIN TUBE INCISION

CROSS REFERENCE TO RELATED APPLICATIONS

This application is a continuation-in-part of U.S. patent application Ser. No. 15/901,166, filed Feb. 21, 2018, (pending); the entirety of which is incorporated by reference herein.

FIELD OF THE INVENTION

The invention relates to methods and devices for the management of body fluids leaking from a surgical drainage incision in a patient.

BACKGROUND OF THE INVENTION

Surgical drains are tubes placed near surgical incisions in the post-operative patient, to remove pus, blood or other fluid (herein collectively referred to as "fluid"), preventing it from accumulating in the body. The type of drainage system inserted is based on the needs of patient, type of surgery, type of wound, how much drainage is expected and surgeon preference. Millions of surgical drains are placed daily in various body cavities and spaces. Placement of surgical drain typically involves making a skin incision matching the size of the drain and subsequently tunneling the drain trough the incision, placement of the drain in the appropriate space according to the application and securing the drain to the skin with sutures. Other methods of securing the drain in place include taping or coiling of the drain inside the cavity. Regardless of the way the drain is placed it is impossible to consistently match the size of the incision to the drain size. In addition, the capacity of the human skin to stretch contributes to size mismatch between the incision size and the drain caliber. The result is a small skin opening around the drain that causes fluid leaks.

Fluid leaks around surgical drain incisions are a consistent problem in surgical units around the world. Leaked fluids have a significant impact on increased use of disposable surgical dressings leading to increased supply cost, increased hospital laundry turnover, significant impact on personnel engagement requiring increased staff presence and occupation in surgical units. Moreover, the leaked fluids may lead to skin irritation and maceration resulting in skin infections that could be extremely serious in some settings. In addition, an open communication with the cavity may lead to infection of subcutaneous tissues and the cavity itself. This requires the continuous use of various skin barriers and protective dressings that need to be changed frequently, thus leading to increasing cost.

Openly leaking fluids challenge the sterility of the surgical site. In addition, leaking fluids increase risk of infection. Both of these problems significantly impact the ability to record proper outputs of the drain placement sites thus influencing surgical decisions and outcomes. From a hospital's perspective in the era of Value Based Purchasing (VBP) this problem turns out to be extremely costly to the hospital. Leaking drains cause surgical/drain site infections, skin infections and irritations lead to readmissions. Patients staying in beds with soaked sheets and gowns report lower level of hospital overall experience and care on surveys decreasing hospital scores and ultimately reimbursement. Patient's and family members experience increased stress and anxiety observing a surgical drain leaking unfamiliar fluids. This leads to perception of poor quality of care, mistrust and tension with physicians and personnel.

Any wound management cost is dependent on three major factors such as cost of supplies, nursing time and extra time patient spends in the hospital. The fourth factor is VBP's patient and family experience and overall hospital score impacting reimbursement.

It is estimated that one gauze dressing change costs $6.36 for the material, $9.14 for nursing service totaling $15.54. It is not uncommon to have dressings changed every hour on a patient with an active leaking drain site.

Accordingly, there is a need for methods and devices that minimize or eliminate the problem of fluids leaking from a surgical drainage incision thereby eliminating the need for frequent dressing changes.

SUMMARY OF THE INVENTION

The foregoing problems are addressed by the method and device for the management of body fluids leaking around a surgical drain in accordance with the invention.

In one aspect the device comprises a fluid collection system. The fluid collection system broadly includes a leaked fluid remover, an adhesive backed wafer for securing the leaked fluid remover to the skin of the patient and a leakage collection pouch for capturing fluid leaked from the surgical drain incision. The leaked fluid remover is positioned over an opening in the wafer. In some aspects, the leaked fluid remover may include a connector or connecting assembly configured to sealably couple onto a mating connector on the adhesive wafer assembly.

In another aspect, the leaked fluid remover may include a housing having a central opening to receive surgical drain tubing, entering from a surgical incision, and a spaced apart coaxial second opening through which the surgical drain tubing passes to exit the leaked fluid remover housing. The second opening may be configured with a fluid-tight elastomeric septum for receiving and sealing around a range of variously sized surgical drain tubing.

Fluids leaked from the surgical incision that have not passed through the surgical drain tube are captured by a leaked fluid remover and diverted to a collector pouch that is in fluid communication with the leaked fluid remover.

BRIEF DESCRIPTION OF THE DRAWINGS

For a better understanding of the invention, and to show how the same may be carried into effect, reference will now be made, by way of example, to the accompanying drawings, in which:

FIG. 9a is a cross-sectional view of an appliance including a leaked fluid remover with an alternative configuration.

FIG. 9b is a perspective view of the appliance of FIG. 9a affixed onto a patient's skin.

DETAILED DESCRIPTION OF THE INVENTION

Figure 1:
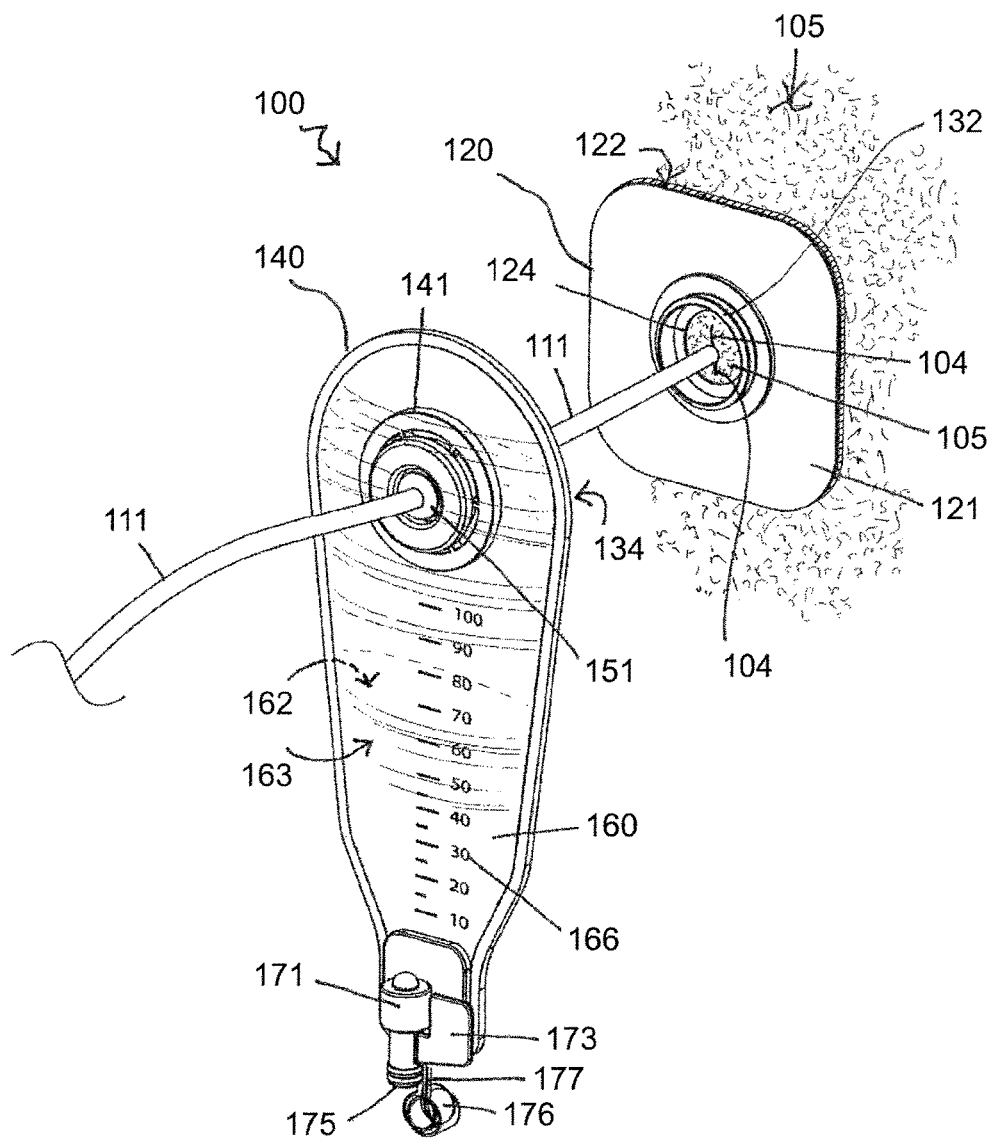
FIG. 1 is a perspective view of the fluid collection system in accordance with an aspect of the invention.

As used herein, leaked fluid means the fluid that leaks around a surgical incision after surgery that is not captured by the surgical drain tubing that is inserted into the incision to aid in removing fluid. Correspondingly, surgical fluid or drained surgical fluid means the fluid that is captured by the surgical drain tubing.

Like elements of the fluid collection system 100 in accordance with the invention are labeled with like reference numerals in the FIGS. and throughout the disclosure.

Figure 2A:
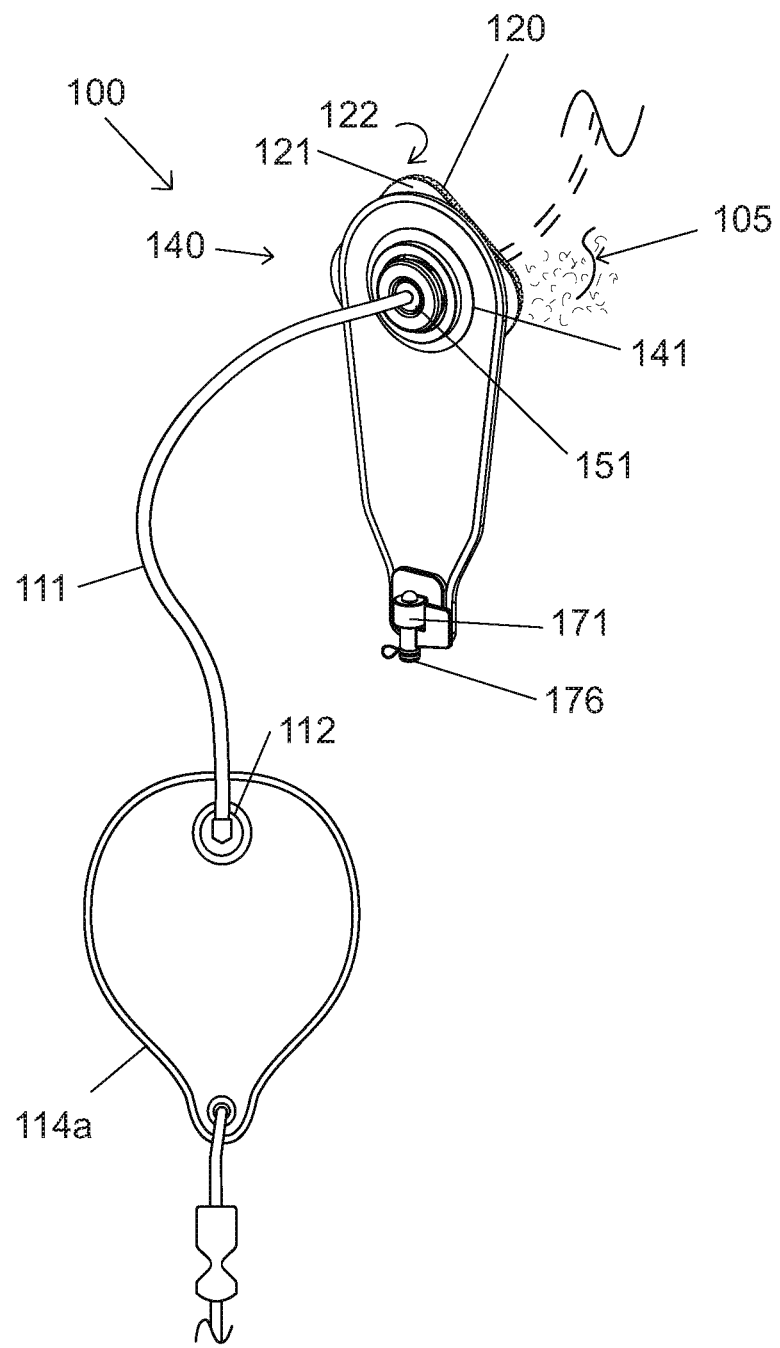
FIG. 2a is a perspective view of the fluid collection system including a drainage collection container in accordance with an aspect of the invention.
Figure 2B:
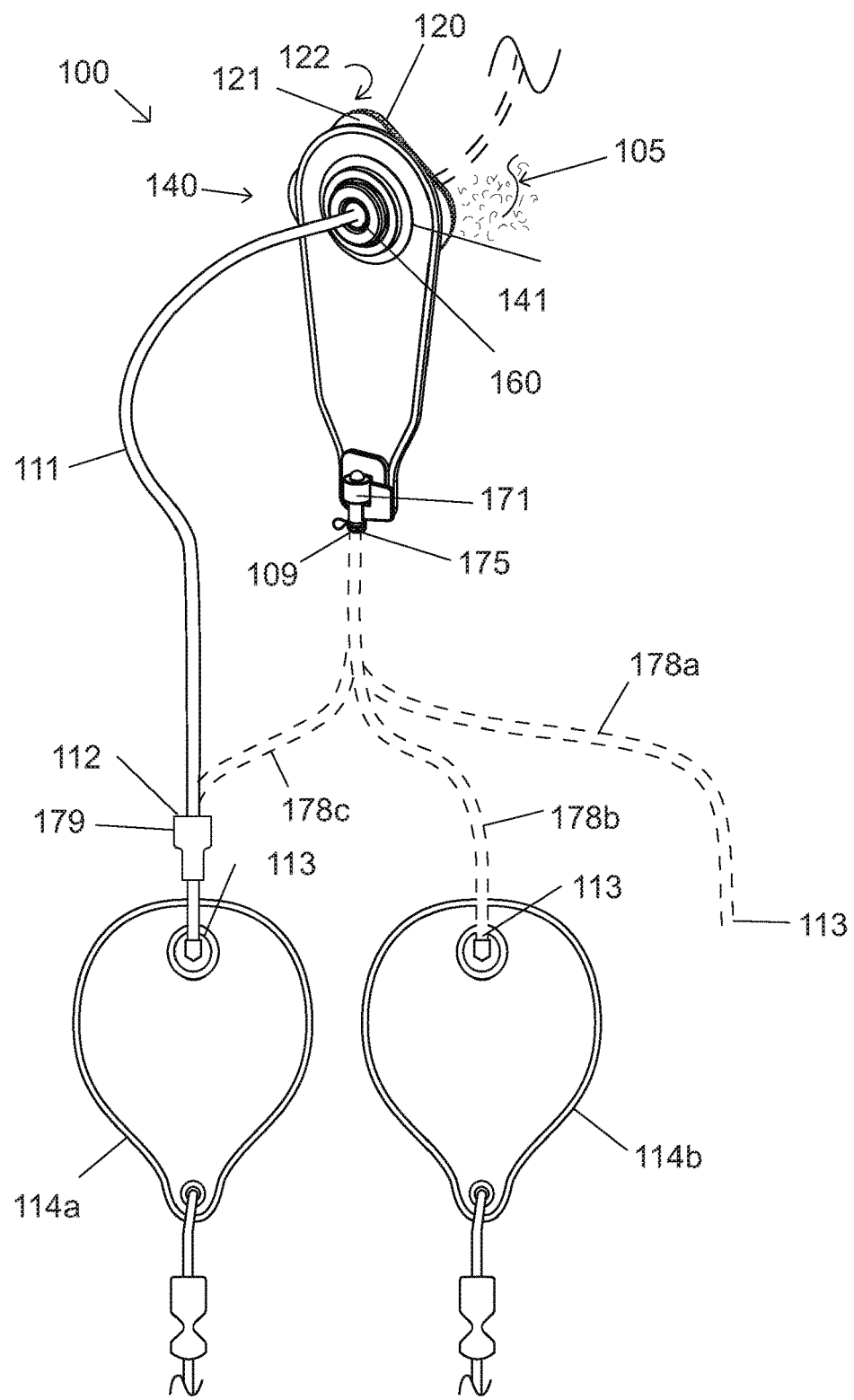
FIG. 2b is a perspective view of the fluid collection system in accordance with an aspect of the invention showing alternative ways for emptying leaked fluid for the leaked fluid collector.
Figure 3:
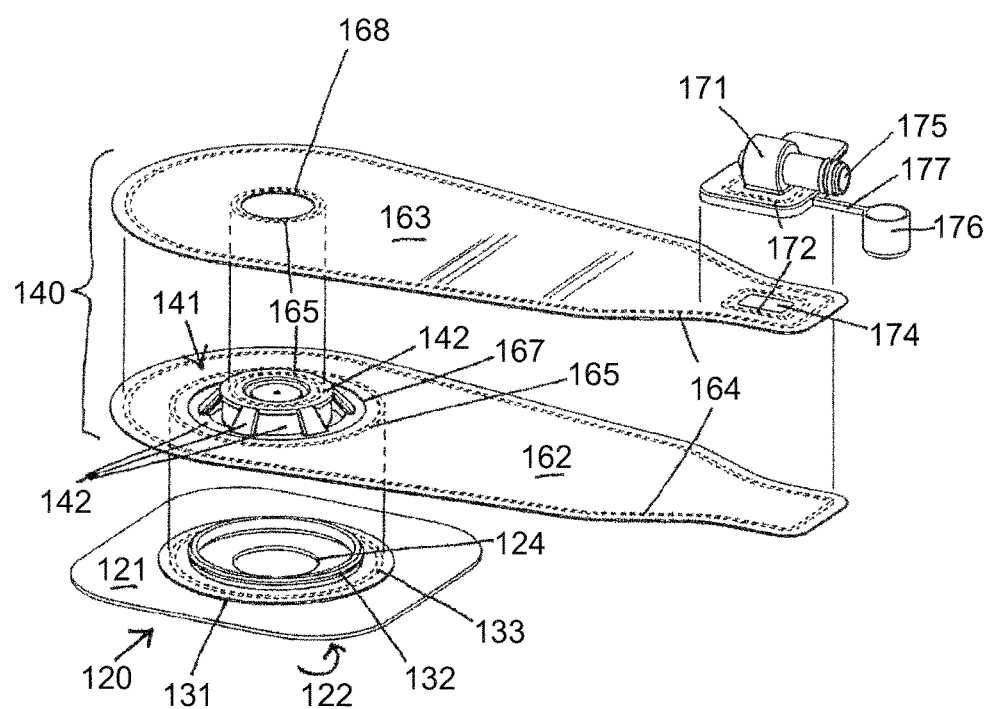
FIG. 3 is an exploded perspective view of the fluid collection system in accordance with an aspect of the invention illustrating the liquid tight seals throughout the system.

Referring generally to FIGS. 1-3, the fluid collection system 100 in accordance with an aspect of the invention is illustrated. Fluid collection system 100 broadly includes baseplate 120 and appliance 140. Fluid collection system 100 may be used in conjunction with other surgical products known to those of skill in the art, including various types of surgical drains and surgical drain containers.

Baseplate 120 includes wafer 121, adhesive backing 122 and a generally centered wafer opening 124. Wafer 121 includes wafer opening 124. In some aspects, a connector 132 may be affixed and generally centered upon the wafer opening 124. The adhesive backing 122 may be constructed of materials that are non-allergenic relative to skin contact, be sufficiently tenacious to remain adhered to skin for several days, and be able to be removed without pain. Such materials may include silicone gel, acrylic, hydrocolloid and other like adhesive materials known to those of skill in the art. Wafer 121 may be constructed of a resilient materials so as to easily deform and flex when adhered to a patient's skin 105. The outer perimeter shape of wafer 121 may be round, square, rectangular, rhombus and other like shapes. In use, the baseplate 120 may be adhesively affixed onto a patient's skin 105 with the wafer opening 124 generally centered upon a surgical drain incision 104 for receiving a surgical drain tubing 111. In this manner, the surgical drain tubing 111 may be anchored with sutures to the skin 105 surrounding the incision 104, as accessible through with the wafer opening 124. Further, the drain tubing 111 may be anchored with tape to the adjacent skin 105 and/or to a portion of wafer surrounding the opening 124 and within the wafer collar 132.

As configured, the fluid collection system 100, enables the wafer opening 124 in a baseplate 120 to be positioned over a previously placed surgical drain tubing 111. Alternatively, if baseplate 120 has been previously adhered to the patient's skin 105 surrounding a surgical incision 104, the drain tubing 111 may be placed through the wafer opening 124 in the baseplate 120. A first end of the surgical drain tubing 111 may be inserted through the surgical incision 104 or wound in the patient's skin 105. The surgical drain tubing 111 may pass through the wafer 121 and, additionally pass through the leaked fluid remover 141.

Appliance 140 includes leaked fluid remover 141. Leaked fluid remover 141 may include a rear facing fluid remover connector 134. The appliance 140 may further be sealably connected to leaked fluid collector 160. Leaked fluid collector 160 may include a forward facing outer film 163 and a rear facing inner film 162. The film material may include any thermoplastic material known to those of skill in the art such as polyethylenes and polyvinylchlorides, which easily adhere and seal to itself and to other thermoplastic injection molded materials, for example by radiofrequency, ultrasonic and/or heat sealing processes. The forward facing outer film 163 may be transparent to facilitate visualization of the color and other characteristics of the leaked fluids by health care professionals while the rear facing inner film 162 may be opaque to assist in visualization of the leaked fluids.

The leaked fluid collector 160 may be generally configured as a pouch. Leaked fluid collector 160 is depicted as having an elongated form so as to more easily visualize the volume of collected fluid within. However, those of skill in the art will appreciate that the leaked fluid collector 160 may have any shape such as square, rectangular, round, conical, cylindrical and the like and such shapes are within the scope of the invention. A graphic scale 166 may be applied, for example by a pad printing process, onto the forward facing outer film 163 to enable a health care professional to discern the relative volume of collected fluids. The scale 166 may, for example, be marked in 10 ml increments up to 100 ml or may comprise any other appropriate scale known to those of skill in the art.

Appliance 140 may be mechanically and fluidly connected onto the baseplate 120, by sealingly coupling the fluid remover connector 134 onto the wafer connector 132, for example, in a snap-fit, quarter turn, bayonet and other types of connectors known to those of skill in the art. Upon coupling, fluids leaked from the surgical incision 104 may pass through the wafer opening 124 via flow path F (best seen in FIG. 4b), and into the leaked fluid remover 141, and then further on into the leaked fluid collector 160.

Generally surgical drain tubing 111 is positioned through the rear of the appliance 140, and then passed through elastomeric septum 151 positioned within leaked fluid remover 141. Surgical drain tubing 111 then exits from the opposing front side of appliance 140. Surgical drain tubing 111 may be positioned through septum 151 from either direction. In this manner, appliance 140 may be coupled onto baseplate 120 after the surgical drain tubing 111 has been placed in the surgical incision 104 or alternatively before the surgical drain tubing 111 is placed in the surgical incision. Advantageously, therefore, appliance 140 may be removed from the surgical drain tubing 111, as necessary, for example, for maintenance of the surgical incision 104 or of the skin 105 surrounding the incision 104 or to replace baseplate 120, or to replace the appliance 140 or any of the component parts without disturbing the surgical drain tubing 111.

The fluid collection system 100 thereby enables uninterrupted draining of detritus from internal organs from a surgical incision 104, through surgical drain tubing 111 that passes axially through leaked fluid remover 141, while the leaked fluid remover 141 simultaneously removes leaked fluid away from surgical incision 104, and diverts it to be captured and collected into leaked fluid collector 160.

Leaked fluid collector 160 may include port 175 at the proximal end thereof. Port 175 is configured to allow a user to drain the leaked fluid from the leaked fluid collector 160. The port 175 may include an openable/closable outlet valve 171 with a valve actuator 173, for example, a lever, collar, knob or paddle. The port 175 may also optionally include a removable cap 176 to prevent dripping of any residual voided matter. Cap 176 may optionally include a tether 177 so as to be affixed adjacent to port 175 for ease of use and accessibility.

Referring now to FIG. 2a a perspective view of the fluid collection system 100 in use is depicted. Fluid collection system 100 is depicted as a closed system used in conjunction with drainage collection container 114a. Appliance 140 is shown coupled to baseplate 120 with a wafer 121 adhesively attached to a patient's skin 105. A length of surgical drain tubing 111 passes through the leaked fluid remover 141 and exits the appliance 140 through the elastomeric septum 151. A second end 112 of the surgical drain tubing 111 is shown connected to a remotely located surgical drainage collection container 114a and is configured to collect drained (non-leaked) surgical fluid. Surgical drain bags are known and are generally positioned away from and below a bed-ridden patient, often, for example, to a bed frame to facilitate optimal passive gravity flow through the surgical drain tubing and into a drainage collection container 114a.

Referring now to FIG. 2b the overall system configuration of FIG. 2a is depicted and shows in dashed lines alternative ways 178a, 178b, 178c leaked fluid may be emptied from the leaked fluid collector 160. Leaked fluid may be emptied from the leaked fluid collector through valve 171 to port 175 where it may be directed into a selected waste container of choice for disposal. A first end 109 of a leaked fluid drain conduit 178a may be connected onto the leaked fluid collector port 175 and a second end 113 routed to a waste container or receptacle of choice (not shown). Alternatively the second end 113 of the leaked fluid drain conduit 178b may be connected onto a secondary drainage collection container, as may be desired to further monitor overall total leaked fluid volume over an extended period of time. Or the second end of the leaked fluid drain conduit 178c may be connected onto a 'Y' connector 179, inserted downstream within the length of surgical drain tubing, such that the leaked fluid may be added to and collected together, along with accumulated surgical drainage.

Referring now to FIG. 3, the locations of basic liquid tight seals throughout the fluid collection system 100 are depicted. Appliance 140 and wafer 120 may be easily assembled using custom fixtures in conjunction with conventional types of ultrasonic, radio frequency or heat sealing methods to achieve liquid tight bonds. As such, components may be manually assembled for low pilot production quantities. Alternatively, the assembly may be automated with web fed film inputs and automated component placements.

Flange 131 is positioned on wafer opening 124 and circumferentially coupled along a peripheral edge to wafer 121 at bond 133. Bond 133 may comprise welding or other methods known to those of skill in the art. Housing 142 and/or the fully assembled leaked fluid remover 141, may also be bonded 165 about its peripheral edge, onto the inner film 162, positioned on center with respect to the inner film opening 167. The sub-assembled valve 171 may be bonded 172 onto the lower extremity of the outer film 163, positioned on center with respect to the valve opening 174. Finally, the outer film 163 may be bonded 165 onto the housing 142, centering the outer film opening 168 about the central axis 144 of the housing, and the outer film 163 may be bonded 164 to the inner film 162, creating a sealed peripheral edge about the leaked fluid collection chamber 169.

Referring now to FIGS. 4-7, cross sectional views of the appliance 140 and fluid collection system 100 are depicted. Each of the components depicted, with exception of the wafer 121 and leaked fluid collector 160, are generally circular in form and radially structured about the central axis 144. Therefore, the sectional views, when showing components in static state, are shown symmetrical left to right, aside from particular features on the circular forms.

Figure 4A:
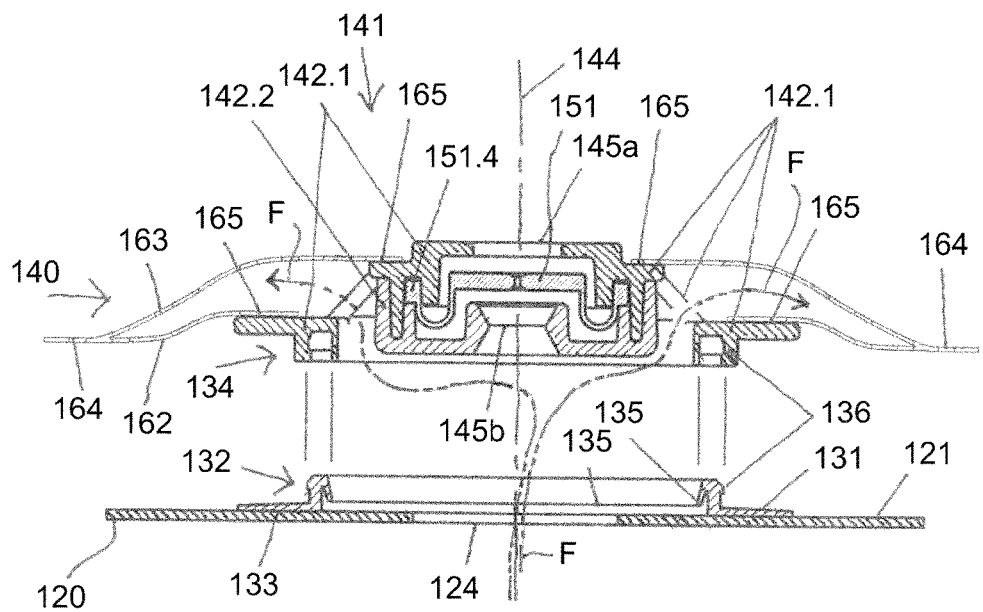
FIGS. 4a and 4b are cross-sectional views of the appliance of the fluid collection system in accordance with an aspect of the invention.

Referring to FIG. 4a, an exploded view of baseplate 120 is shown below appliance 140. In various aspects, the baseplate 120 includes a circumferential wafer connector 132 with a radially disposed wiper seal 135 around its inner surface, both integrally molded upon a flange 131. In various aspects, the flange 131 may bonded or heat sealed to flexible wafer 121 and centered on a wafer opening 124.

Appliance 140 broadly includes leaked fluid remover 141 and septum 151 positioned within housing 142. Those of skill in the art will appreciate that housing 142 may be injection molded and may comprise a single part or two or more parts. A two part housing 142 includes housing component 142.1 and a housing component 142.2, configured to house a septum rim 151.2 therewithin. Housing components 142.1 and 142.2 may be joined, for example, with mating snap fit structure, ultrasonic welding, or adhesive bonding. In other aspects a housing 142 provides a structure used to interconnect adjacent spaces and components in functional relationships. In other aspects, the housing includes a pair of spaced apart circular platform surfaces for film to housing bond 165, one for sealably bonding the outer film 163 and the other for the inner film 162.

Figure 6:
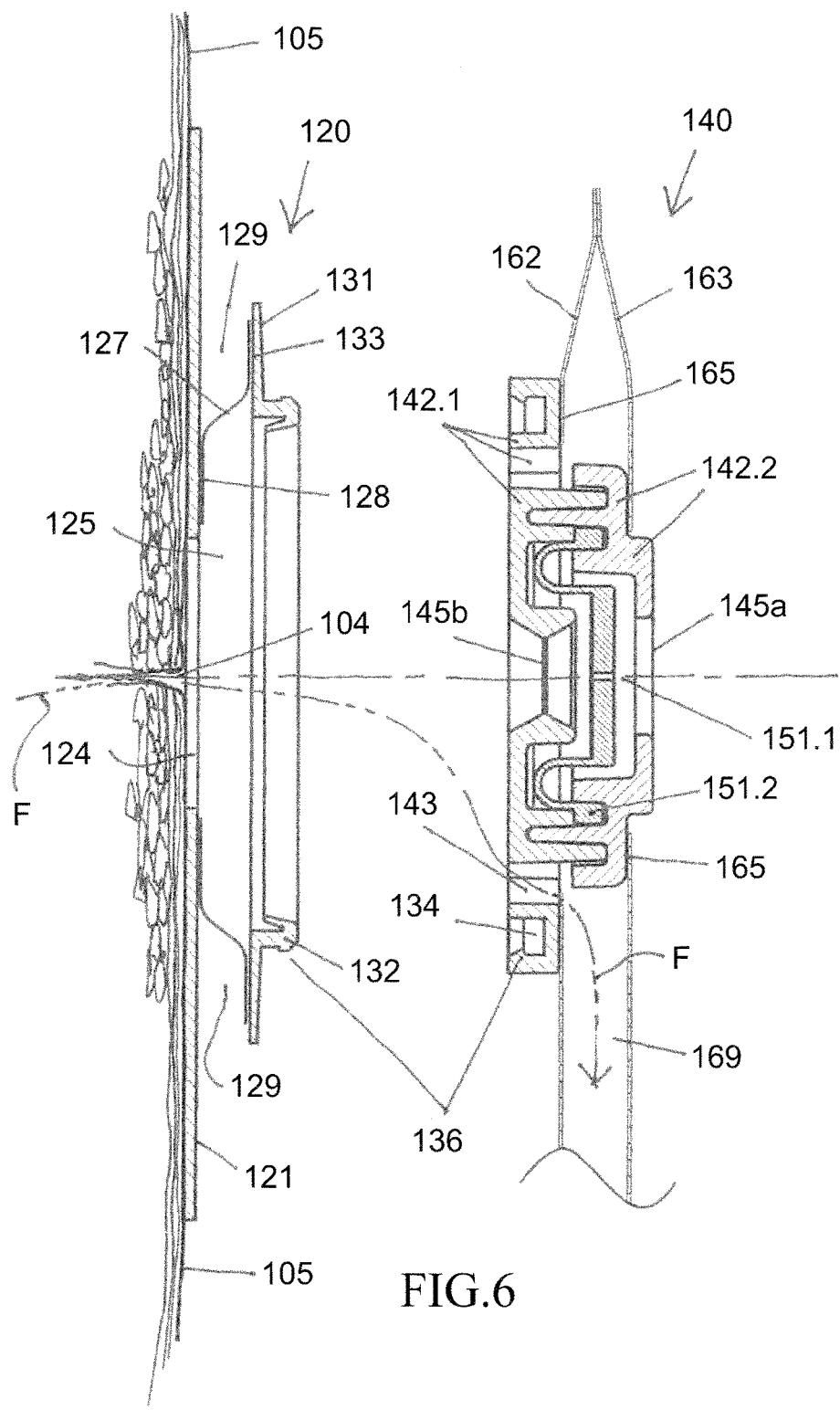
FIG. 6 is a cross sectional view illustrating another aspect of the fluid collection system in accordance with the invention.

Housing 142 is depicted as a structural body comprised here, for example, of two injection molded thermoplastic housing components 142.1 and 142.2. One of ordinary skill in the art will appreciate that such a structural body with such particular functions may be configured in a variety of different ways and still fall within the scope of the invention. For example, in some aspects, looking closely at the cross hatching of housing components 142.1 and 142.2, housing component 142.1 includes a fluid remover connector 134, a leaked fluid remover opening 145*a* (above the septum) and a film to housing bond 165 for both the inner film 162 and for the outer film 163. Mating component 142.2 includes a leaked fluid remover opening 145*b* (below the septum) and captures the septum rim 151.2 from below. In other aspects, and as best seen in FIG. 6 an alternative structural embodiment for housing 142 is shown. Component 142.1 includes a fluid remover connector 134 and a film to housing bond 165 for the inner film 162. However, the film to housing bond 165 for the outer film 163, as well as the leaked fluid remover opening 145*a* (above the septum), are now both instead positioned on mating component 142.2. Further, leaked fluid remover opening 145*a* (above the septum) and the film to housing bond 165 for the outer film 163 are now part of the mating component 142.2. These and other design variations may be conceived, for example, to optimize molding, manufacturing, heat sealing and/or assembly sequences.

Referring again to FIG. 4*b*, baseplate 120 and appliance 140 are shown matingly coupled by wafer connector 132 and fluid remover connector 134. Fluid remover connector 134 is inset as a mating circular channel into the lower portion of housing 142. Circular ring-shaped wafer connector 132 extends radially upward from flange 131 and couples to fluid remover connector 134 in a snap-fit arrangement. Those of skill in the art will appreciate, however, that couplings other than snap fit arrangements may be used. Mating mechanical interlocks 136 engage the connector components in assembly. Hoop stress, inherent in mated circular connector components 132 and 134, which are injection molded with selected thermoplastic materials, facilitate a secure yet releasable attachment, as well as an intimate fluid tight interference fit upon wiper seal 135. Baseplate 120 and appliance 140, when coupled together in this manner, create a fluid flow chamber 143 for fluid leaked from a surgical incision to flow into and through a leaked fluid remover 141 and onward to be captured and collected within leaked fluid collector 160 through flow path F.

Elastomeric septum 151 housed within housing 142 is molded, for example, in highly elastic silicone or thermoplastic elastomer, such as 20 to 30 Shore A. Septum orifice 151.1 is generally centered on septum 151 and may also be generally centered upon the central axis 144 of housing 142 when in a static state. The septum orifice 151.1 may be generally round, cylindrical or frustoconical through its length and may be sized to a internal diameter that is smaller than the surgical drain tubing 111 for which it is intended to be used. Those of skill in the art will appreciate that various septum 151 sizes may be provided depending on commercially available outer diameters of surgical tubing. It is contemplated, therefore, that a range of appliance 140 products may be made available, each with variously sized septums 151.

Alternatively, a single appliance 140 may include a small quantity of easily interchangeable alternately sized septums 151, each intended for use in conjunction with various types of surgical drain tubing 111 or for specific types of procedures. For example, one septum orifice 151.1, with a diameter of approximately 2.3 mm/0.09", may be useful to achieve a positive interference fit around surgical drain tubing 111 intended for use to drain abscesses, for which surgical drain tubing 111 typically ranges in diameter from 2.7 mm/8 French up to 4.7 mm/14 Fr in diameter. Septum orifices 151.1, of other sizes may be intended for other specific surgical applications, for example, a septum orifice of approximately 8 mm diameter, may be useful for chest/bronchial procedures, for which surgical drain tubing typically ranges from approximately 9.3 mm/28 Fr up to approximately 11.3 mm/34 Fr. Alternatively, as another example, fluid collection devices 100 may be offered with two or more alternately sized septums 151, with differently sized orifices 151.1—ranging from a smaller size of approximately 2.3 mm diameter to a larger of approximately 5 mm diameter, so as together, a sealed fit may be achieved upon surgical drain tubing 111 needed for small abscesses up to those needed for larger chest/bronchial procedures—typically ranging up to approximately 34 Fr/11.3 mm diameter.

Septum 151 may include integrally molded thick and thin sections and alternative feature geometries to achieve specific functions. In other aspects, a generally circular elastomeric septum 151 may be captured, about a circumferential rim 151.2, between mating injection molded housing 142 components to achieve a fluid seal closure of a leaked fluid remover aperture 147*a*. In other aspects, the septum 151 includes a highly elastic septum orifice 151.1, with ability to stretch to receive and yet remain sealed around a range of surgical drain sizes. The septum orifice 151.1 is centered within a stiffer septum body 151.3. A highly flexible septum diaphragm 151.4 surrounds the stiffer septum body 151.3, enabling the stiffer septum body 151.3 to move about radially, axially and/or pivotally, so as to alleviate side load tension upon the septum orifice 151.1—caused, for example, by pulling upon a surgical drain passing through the septum orifice 151.1—as may otherwise induce a leaking situation should the septum orifice 151.1 become elongated. In other aspects, the septum diaphragm 151.4 and septum body 151.3 are enclosed within a loosely fitting septum space 152, as may be used to controllably limit axial and radial and/or pivotal movements of the septum body 151.3.

Figure 4B:
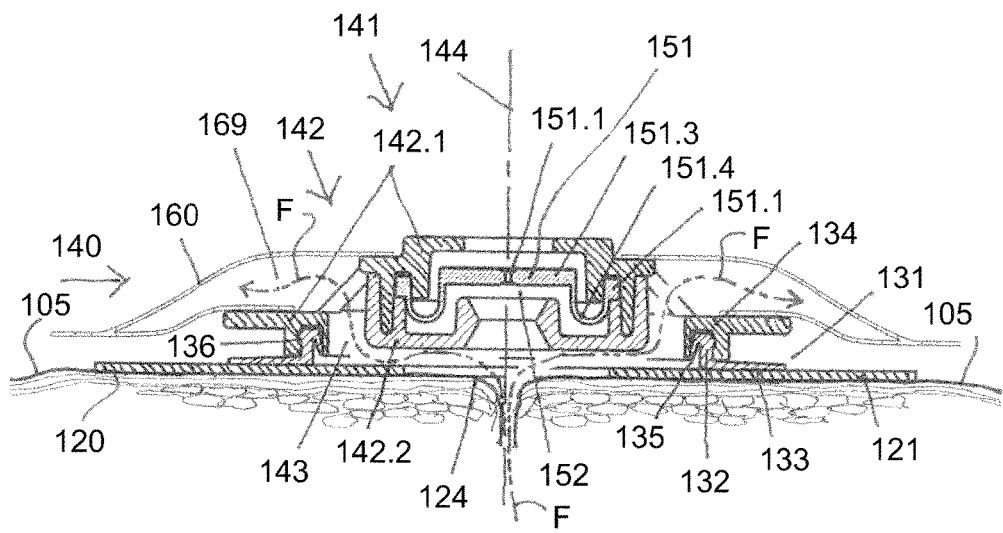
Figure 5A:
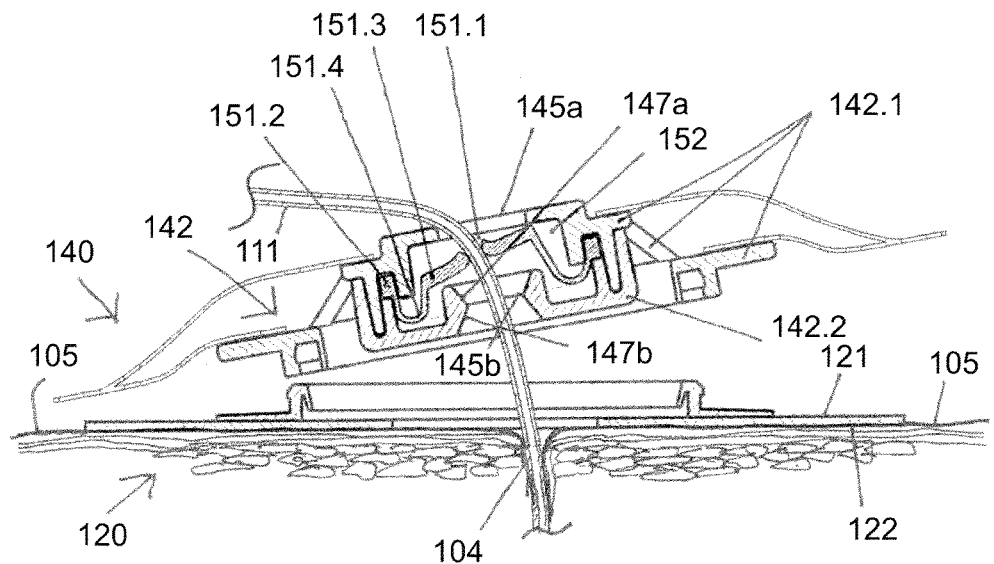
FIGS. 5a and 5b are perspective views illustrating the dynamic radial movement of the elastomeric septum of the appliance in accordance with an aspect of the invention.
Figure 5B:
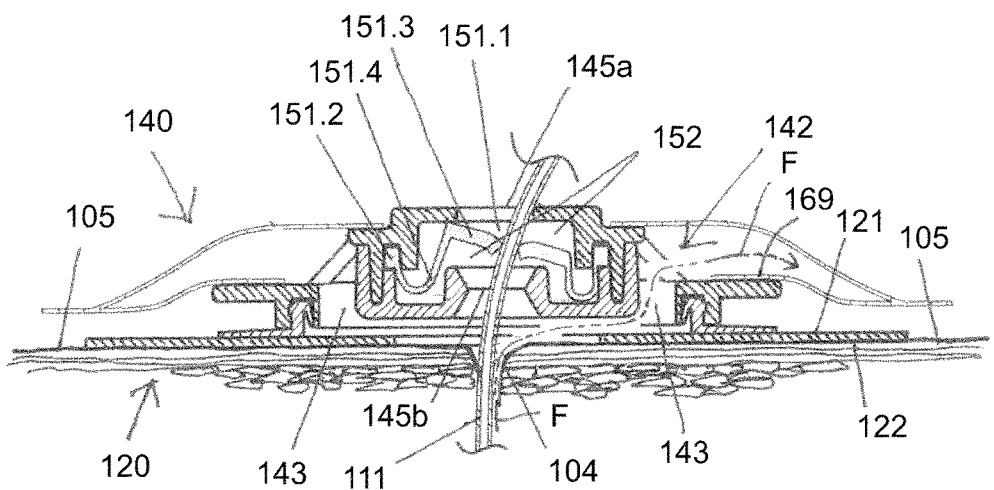

Appliance 140 is presented in FIGS. 4*a* and 4*b* in static state and in FIGS. 5*a* and 5*b* in a dynamic state to illustrate and describe dynamic inner functions of the fluid collection system 100, which have only been generally described through earlier FIGS. With reference to both FIG. 5*a* and FIG. 5*b*, a fluid collection system 100 is illustrated in situ, with wafer 121 affixed by adhesive backing 122 to a patient's skin 105. The septum orifice 151.1 is shown stretching to accommodate variously sized surgical drain tubing 111. The septum body 151.3 is shown as it may move about axially, radially and/or pivotally within the confines of a septum space 152.

Referring to FIG. 5*a*, appliance 140 may be installed or replaced over surgical drain tubing 111 which has previously been placed through a surgical incision 104. Similarly, appliance 140 may be uncoupled from a base-plate 120 and further removed over the second end of the surgical drain tubing 111, without replacing or disturbing the surgical drain tubing 111—as may be needed, for example, to clean or treat the surgical incision 104 and/or the adjacent area of patient's skin 105. Additionally, appliance 140 may be removed as necessary to ease replacement of a surgical drain tubing 111, without need to remove the base-plate 120 from the patient's skin 105.

As previously noted, surgical drain tubing 111 may be inserted through appliance 140 from either direction, i.e. from the top of the appliance 140 or from the bottom. The housing 142 therefore may include two leaked fluid remover openings 145, namely an outer facing opening 145*a*, above the septum 151 and an inner facing opening 145b, below the septum 151. Both openings 145a, 145b may be of approximately the same size and to clear the largest size surgical drain tubing 111 for which the appliance 140 may be intended. 34 Fr/11.3 mm surgical drain tubing 111 for chest/bronchial procedures are typically the largest used. Therefore, such openings 145 may range in size up to about 12 or 14 mm diameter. Whereas the septum orifice 151.1, through which a user needs to insert surgical drain tubing is visible to the user through an outward facing opening 145a, the inner facing opening 145 b and associated septum orifice 151.1 are essentially hidden below. Therefore, an inner facing opening 145b may include a bi-directional inner funneled passage 147a and outer funneled passage 147b to assist in guiding surgical drain tubing through a septum orifice.

Referring again to both FIGS. 5a and 5b, those of skill in the art will appreciate that it is important that pulling on the surgical drain tubing 111 does not induce a leak from the appliance 140 by elongating the septum orifice 151.1 through which it passes, particularly in regard to smaller diameters of drain tubing 111 passing through a larger outer facing opening 145.1. Therefore, the sizing of the leaked fluid remover openings 145 may be coordinated relative to the size of the smallest intended surgical drain tubing 111 and the radial movement of the septum orifice 151.1 as controllable within the septum space 152. That is to say, if a pulling force be applied upon the surgical drain tubing 111, relative to the fixed position of housing 142, the force will be generally transmitted through the septum orifice 151.1. If the outer perimeter of a septum orifice 151.1 were to be fixed in position—for example to a housing 142, or for example within a septum body 151.3 that may be fixed in position to a housing 142—then a radially applied pulling force upon the surgical drain tube 111 could cause the elastomeric septum orifice 151.1 through which it passes to stretch, distort and elongate. A deformed and elongated septum orifice 151.1 may become sufficiently enlarged as to enable fluid to escape outward from the fluid flow chamber 143, flowing between the surgical drain tubing 111 and the inner perimeter of the distorted septum orifice 151.1.

To alleviate such a potential leakage problem, a leaked fluid remover 132 may include a particularly configured septum 151. An elastomeric septum orifice 151.1 may be generally centered within an outer facing opening 145a and also generally centered upon and contained within a septum body 151.3, which in turn may be generally centered within a flexible elastomeric diaphragm, which in turn may be affixed within a housing 142, for example with a septum rim 151.2 clamped between housing components 142.1 and 141.2 of a housing 142.

As generally shown in FIGS. 5a and 5b, an elastomeric septum diaphragm 151.4, may enable a septum body 151.3 and an accompanying septum orifice 151.1 to move about together within a septum space 152—in the direction of a pulling force upon surgical drain tubing 111 passing through the septum orifice 151.1.

If a leaked fluid remover 141 is configured for use with a defined/limited range of variously sized surgical drain tubing 111, the smallest sized tubing 111 will inherently move about radially further than larger surgical drain tubing 111, within the outer facing opening 145a of the leaked fluid remover 141.

Therefore, the amount of radial movement of the septum body 151.3 enabled within the septum space 152 should be greater than the amount of radial movement of the smallest diameter surgical drain tubing 111 enabled within the outer facing opening 145a. In such manner, when pulled upon radially, the surgical tubing 111 will become supported against the peripheral edge of the outer facing opening 145a prior to the septum body being supported against the peripheral edge of the septum space—so as to limit pulling of the surgical drain tubing 111 upon the septum orifice and thereby abate elongation of septum orifice 151.1 and consequential leakage from the fluid flow chamber 143.

In at least one aspect, the septum orifice 151.1, the septum body 151.3, the septum diaphragm and septum rim may be a single integrally molded component. In other aspects the septum features may be produced as an assembly. In yet another aspect, the elastomeric septum orifice 151.1 and the elastomeric septum diaphragm 151.4 may be injection overmolded or two-shot molded onto a plastic septum body 151.3.

Referring now to FIG. 6, the fluid collection system 100 is shown oriented vertically to more clearly depict how leaked fluid will passively flow with gravity from a surgical incision 104, through a fluid flow channel 143 and into a leaked fluid collection chamber 169. Cross sectional exploded view depicts appliance 140 spaced apart from baseplate 120, which is affixed on a patient's skin 105 by the adhesive backing 122 of wafer 121. This baseplate 120 is alternatively configured to include, what is commonly referred to in ostomy products as, an accordion 125. Accordion 125 broadly includes accordion flange 127 and accordion flange bond 128. Accordion 125 in this application is typically circular, formed of flexible film that includes a center opening corresponding with a wafer opening 124 and is heat seal bonded 133 about an outer peripheral edge of wafer 121 and along an inner peripheral edge to the peripheral edge of wafer opening 124. In this manner, the peripheral outer edge of wafer 121 may be spaced away from the wafer so as to create a finger clearance space 129 below the accordion flange 127 with which to more easily engage wafer connector 132 on the fluid remover connector 134. As can be seen, the fluid flow path F of the leaked fluid exits the patient's skin through the wafer opening 124 and flows into the fluid flow chamber 143 and out to the leaked fluid collector chamber 169 and eventually to the leaked fluid collector 160.

Referring now to FIG. 7 another aspect of the invention is shown. Leaked fluid remover 141 now includes a septum 151 with a mating elastomeric pressure seal 155, placed on the same axis as the elastomeric septum 151. This feature advantageously allows the surgical drainage tube 111 to be removed, for example in a variety of patient care settings such as during the patient's hospital stay or when the patient returns home. The elastomeric pressure seal 155 prevents leaking of the leaked fluid and ensures that it exits into the leaked fluid collector 16 via flow path F as hereinafter described.

A surgical incision 104 may need to remain open after removing the surgical drain tubing 111 until leaked fluid ceases to flow. Without a surgical drain tube 111 passing through the septum orifice 151.1, a non-occluded septum orifice 151.1 could potentially leak fluid from the appliance 140. Inclusion of an elastomeric pressure seal 155, such as a one-way duckbill type valve, can work in tandem with an elastomeric septum orifice 151.1 to occlude flow in the absence of a surgical drain tube 111. While an elastomeric septum type valve may be defeated in the absence of an occluding surgical drain tube 111, an elastomeric duck-bill type pressure seal may be defeated upon insertion of a surgical drain tube 11*i*. However, together, they assure a secure seal is maintained both with and without surgical drain tube 111.

Figure 7A:
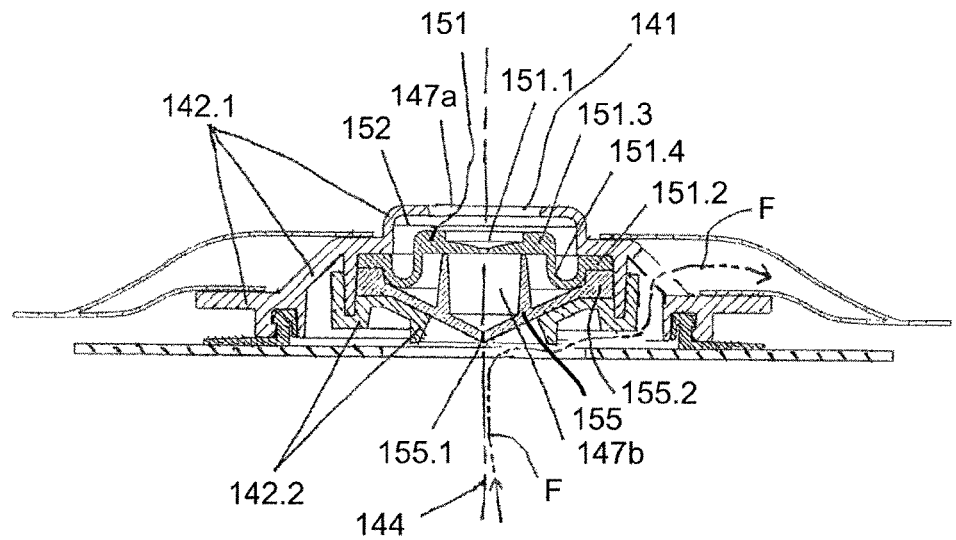
FIGS. 7a and 7b are cross sectional views of the fluid collection system in accordance with an aspect of the invention illustrating a static state and dynamic state, respectively, of the elastomer pressure seal.
Figure 7B:
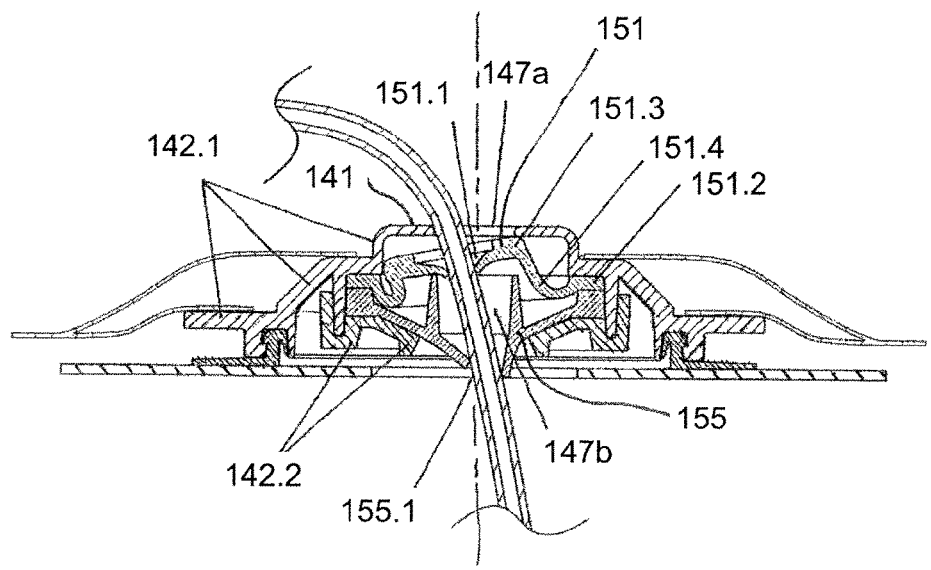

As shown configured, for example, in FIG. 7*a* in static state and in FIG. 7*b* in dynamic state, elastomeric septum 151, with a septum orifice 151.1 and with a septum body 151.3 may be configured to function within a septum space 152—in similar manner as previously described—in conjunction with an elastomeric pressure seal 155, with a pressure seal aperture 155.1 and with an alternatively configured funneled passage 147*b*, with both positioned along a common central axis 144. Septum 151 may be sealably captured upon a septum rim 151.2 and the pressure seal sealably captured upon a mating pressure seal rim 155.2, both captured together between a first housing component 141.1 and a second housing component 141.2.

Figure 8:
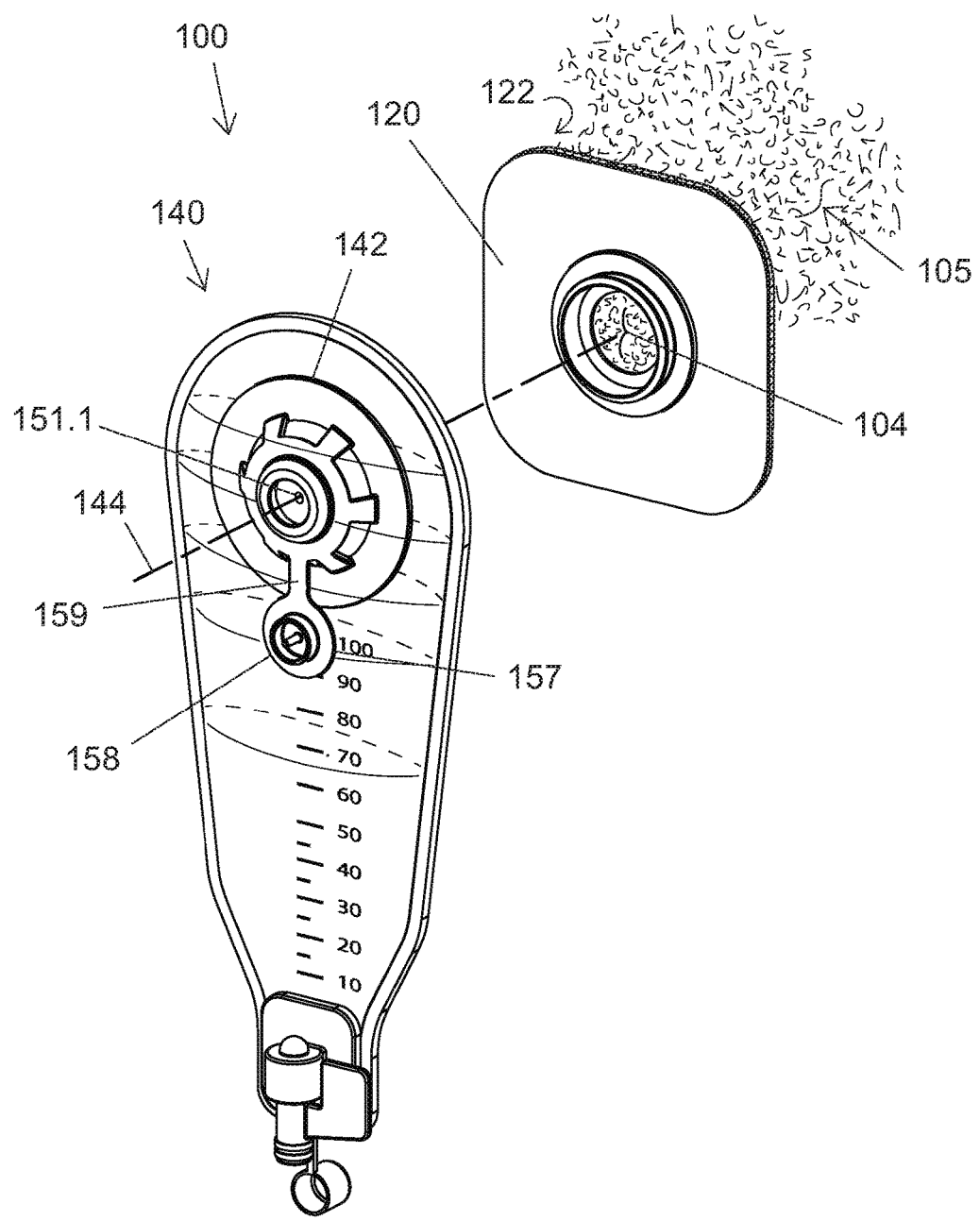
FIG. 8 is a perspective view of one aspect of a leaked fluid remover in accordance with the invention showing a septum orifice plug.

In other aspects of the invention, other methods may be implemented to achieve a sealed appliance 140 in the absence of a surgical drain tube 111. Referring to FIG. 8, a septum orifice plug 158 is shown. Septum orifice plug 158 is sized and configured to press fit into an open septum orifice 151.1. Septum orifice plug 158 may, for example, include a fluid remover cap 157, connected, for example, by cap tether 159 onto the housing 142 of appliance 140. Those of skill in the art will appreciate that all or portions of these components may be integrally molded. In such manner the septum orifice plug 158 may be readily available and appropriately positioned to be inserted along a central axis 144 into an open septum orifice 151.1 in the absence of a surgical drain tubing 111.

Referring now to FIG. 9*a*, appliance 940 including a leaked fluid remover 941 is shown alternatively configured with an outlet port 949 in lieu of an affixed leaked fluid collector 960, for example without an inner film 962 or outer film 963. As such, the leaked fluid remover 941 is comprised, as previously described, of housing 942, including a housing component 942.1, sealably connected to a housing component 942.2, together sealably capturing a septum 951 about a septum rim 951.2; with the septum 951 functioning similarly in regard to having a septum orifice 951.1, a septum body 951.3 and a septum diaphragm 951.4; an outer facing opening 945*a* and an inner facing opening 945*b*; a funneled passage 947*a* and 947*b*; a fluid flow chamber 943 and a fluid remover connector 934 which couples in like manner onto wafer connector 933 on base-plate 920 with a flange 931 on a wafer 921 with adhesive backing 922 and a center opening 924. This appliance 940 differs from previously described embodiments, relative to its housing 942 fully enclosing a fluid flow chamber 943 and having an outlet port 949 with which this leaked fluid remover 941 may be coupled via a leaked fluid collection conduit 978 to, for example, a drainage collection container 914.

The embodiment of an appliance 940 as described in FIG. 9*a* is shown more generally in FIG. 9*b*. As such, this appliance 940 is coupled onto a base-plate 920, shown with a wafer 921 and affixed by adhesive backing 922 onto a patient's skin 905. The appliance has a fluid outlet port 949, onto which a leaked fluid collection conduit 978 may be connected to divert removed leaked fluids through, for example, a 'Y' connector 979, to be accumulated along with drained surgical fluid emitted from surgical drain tubing 911.

Figure 10A:
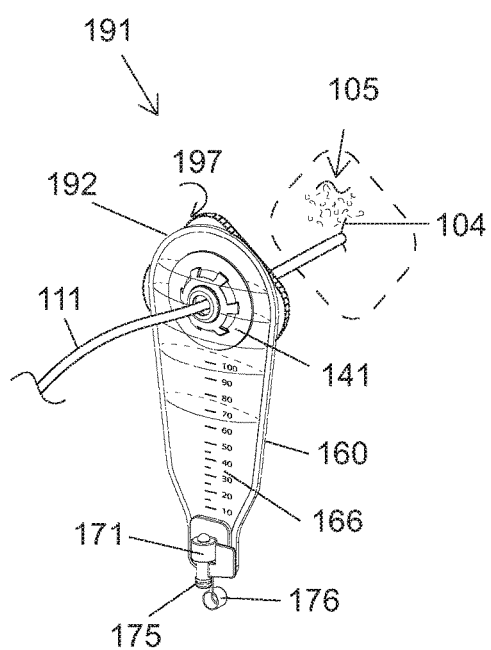
FIGS. 10a and 10b are perspective views of the fluid collection system in accordance with the invention illustrating other ways to couple the appliance to a patient.
Figure 10B:
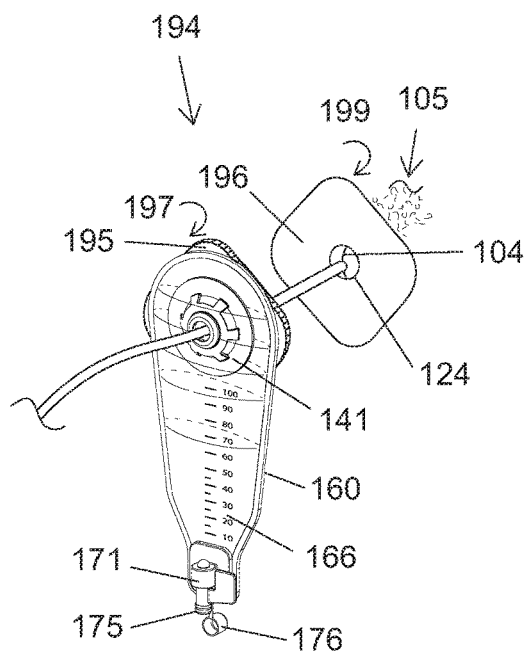

Referring now to FIGS. 10*a* and 10*b*, alternative methods of affixing a fluid collection system 100 onto a patient's skin 105 are provided. In FIG. 10*a*, a one-piece adhesive affixed system 191 is shown. The one-piece adhesive system includes a adhesive backed pad that is applied directly against the patient's skin. FIG. 10*b* depicts a two-piece adhesive affixed system 194. Pad 195 includes an adhesive back 197. Adhesive back 197 is applied to wafer 196 which also includes an adhesive back 199 that is applied to a patient's skin 105. Wafer 196 may have a smooth outer face upon which pad 195 may be adhered. The pad 195 with adhesive back 197 is applied to the wafer 196 making the two-piece adhesive affixed system 194 easily removable when necessary.

Referring now to FIGS. 11*a*-11*d* an alternative embodiment of the appliance 1100 in accordance with the invention is depicted. Like features are labeled with like reference numerals. The appliance 1100 depicted in FIGS. 11*a*-11*d* does not show the baseplate 120, wafer 121, adhesive backing 122 and connector 132 coupled thereto. However, the baseplate system 120 is a previously disclosed hereinbefore and is best seen in FIG. 3.

Appliance 1100 broadly includes leaked fluid remover 1110 having an outer septum 1112 and an inner septum 1114 positioned within housing 142. Housing 142 is the same as housing 142 of FIGS. 1-10 hereinbefore disclosed. Those of skill in the art will appreciate that housing 142 may be injection molded and may comprise a single part or two or more parts. A two part housing 142 includes housing component 142.1 and housing component 142.2. Housing components 142.1 and 142.2 may be joined, for example, with mating snap fit structure, ultrasonic welding, or adhesive bonding. As shown two part housing 142.1, 142.2 is matingly joined by threaded fasteners 1118. In other aspects housing 142 provides a structure used to interconnect adjacent spaces and components in functional relationships. In other aspects, the housing includes a pair of spaced apart circular platform surfaces for film to housing bond 165, one for sealably bonding the outer film 163 and the other for the inner film 162.

Housing 142 is depicted as a structural body comprised here, for example, of two injection molded thermoplastic housing components 142.1 and 142.2. One of ordinary skill in the art will appreciate that such a structural body with such particular functions may be configured in a variety of different ways and still fall within the scope of the invention. For example, in some aspects, looking closely at housing components 142.1 and 142.2, housing component 142.1 includes a fluid remover connector 134, a leaked fluid remover opening 145*a* (above the outer septum 1112) and a film to housing bond 165 for both the inner film 162 and for the outer film 163. Mating component 142.2 includes a leaked fluid remover opening 145*b* (below the septum). In other aspects, an alternative structural embodiment for the housing 142 of appliance 1100 may include a film to housing bond 165 for the outer film 163, as well as the leaked fluid remover opening 145*a* (above the septum positioned on mating component 142.2 similar to that seen in FIG. 6. These and other design variations may be conceived, for example, to optimize molding, manufacturing, heat sealing and/or assembly sequences.

Figure 11A:
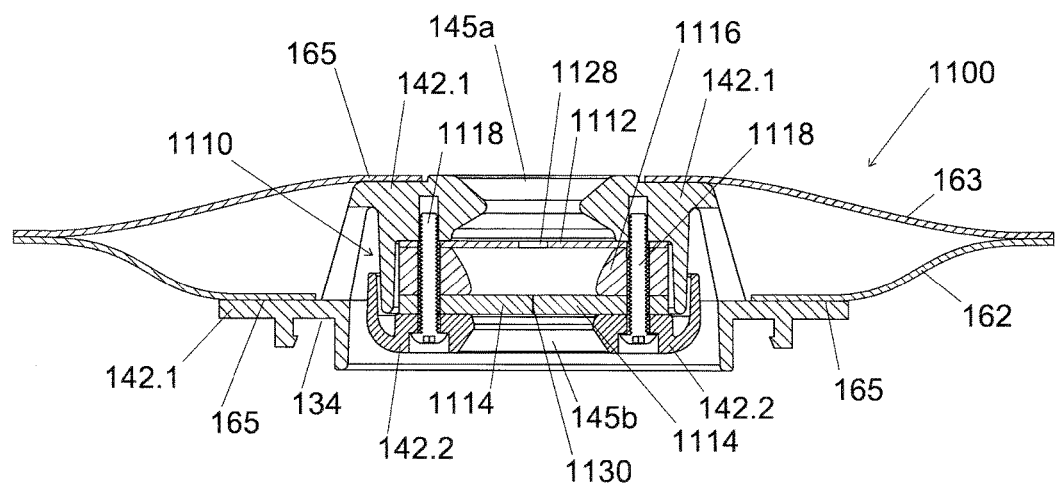
FIG. 11a is a cross-sectional view of an alternative appliance or leaked fluid remover used with the fluid collection system in accordance with the invention in a static position.
Figure 11B:
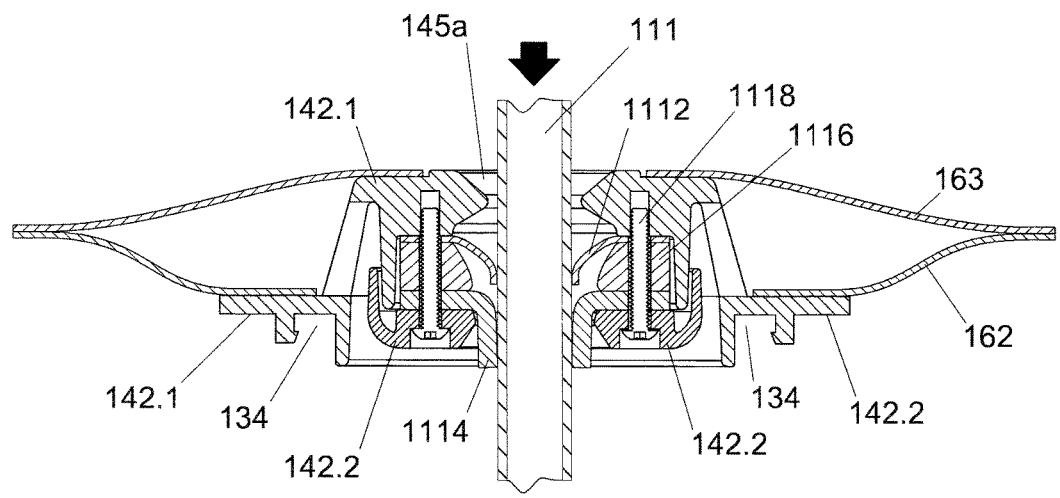
FIG. 11b is a cross-section view of the appliance/leaked fluid remover of FIG. 11A depicting fluid flow through the front side of the appliance and into the patient.
Figure 11C:
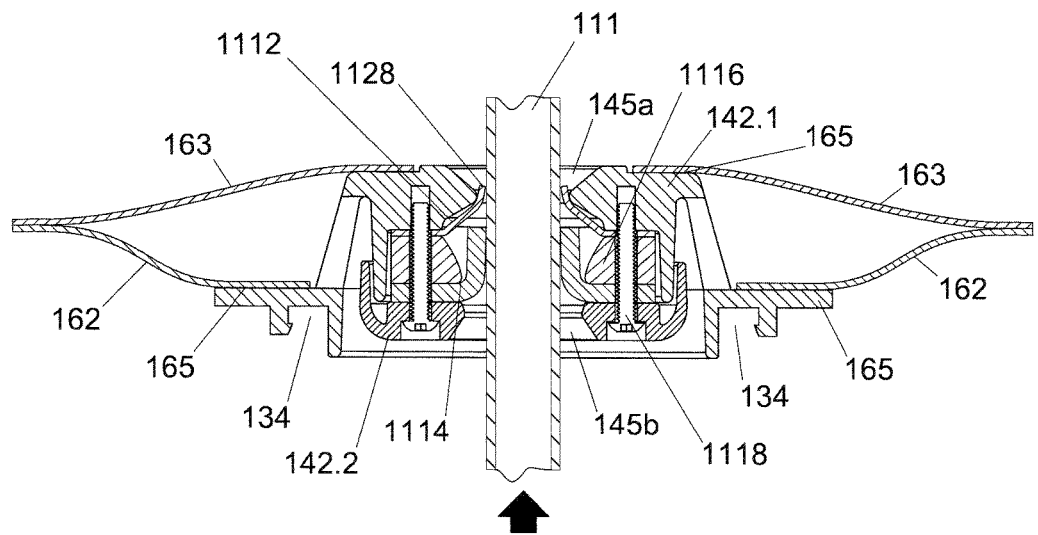
FIG. 11c is a cross-sectional view of the appliance of FIG. 11a depicting fluid flow through the back side (or patient side) of the appliance exiting out to a collection bag.
Figure 11D:
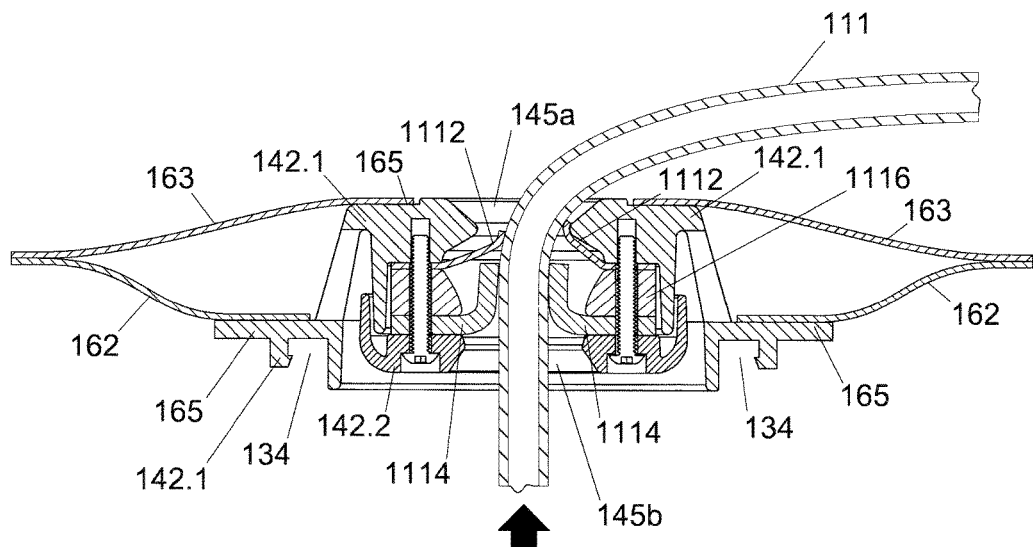
FIG. 11d is a cross-section view of the device showing surgical tubing and fluid flow exiting through the patient side of the appliance showing the septum capable of moving about radially, axially and/or pivotally to alleviate side load tension on the septum caused by displacement of the surgical drain tube.

Appliance 1100 includes spacer 1116, which includes an upper spacer surface 1120 and a lower spacer surface 1122. The lower surface of outer septum 1112 is positioned on or integrally formed with upper spacer surface 1120 while the upper surface of inner septum 1114 is positioned on or integrally formed with lower spacer surface 1122. Spacer 1116 is configured to space apart inner and outer septums 1112, 1114 providing space between the two septums that enable the septum lips 1124, 1126 to splay up and down as the surgical drain tube is inserted from one direction or the other, without the flexed lips 1124 of the outer septum 1112 interfering with the flexed lips 1126 of the inner septum 1114 and vice versa as best seen in FIGS. 11b-11d.

Those of skill in the art will appreciate that spacer 1116 may be constructed of elastomeric or plastic materials. Spacer 1118 may be molded as a separate component or may be an integrally formed as part of either or both septums.

Outer septum 1112 and inner septum 1114 may be constructed of elastomeric materials such as thermoplastic elastomers, silicone and the like. The elastomeric inner and outer septum may be compliant, for example having a durometer of approximately 20-40 shore A, so as to adapt to the diameter of a passed through surgical drain tube 111.

Figure 11E:
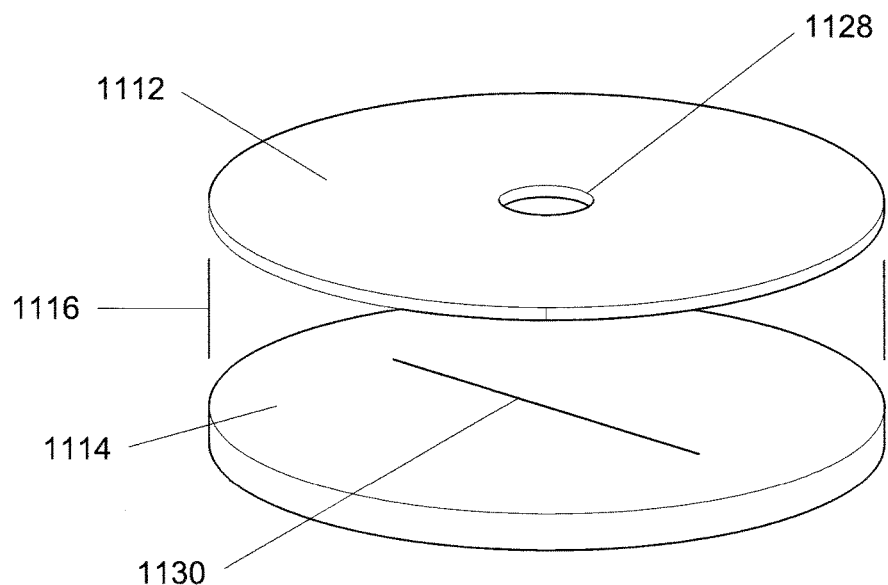
FIGS. 11e and 11f are partial perspective views of an alternative embodiment with spaced apart inner septum with slit and outer septum with opening, shown respectively without and with a passed through drain tube.
Figure 11F:
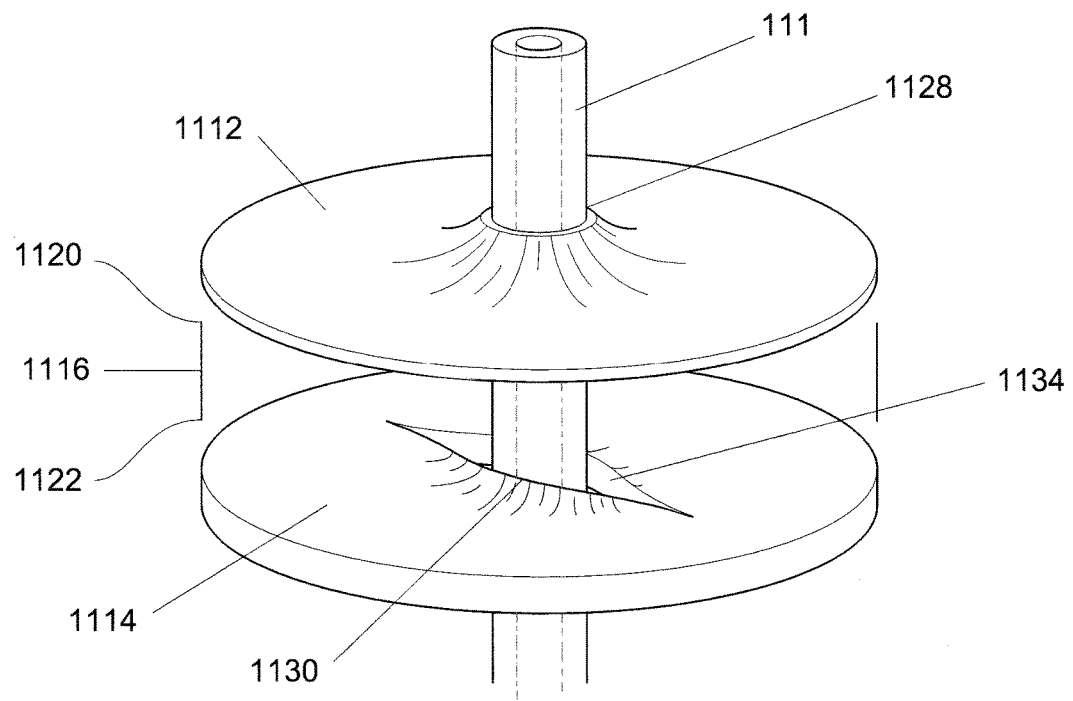

Referring to FIGS. 11e and 11f, an outer septum 1112 includes a generally centered opening 1128 punched, molded, or cut through the body of outer septum 1112. The opening 1128 may be produced in various diameters, each sized to stretch around a defined range of max to min diameter surgical drain tubes 111. The opening 1128 through the outer septum 1112 is preferably circular, thin, and compliant so as to sealably contain an air and fluid tight seal upon the fluid flow chamber 143 when the opening 128 is penetrated by a surgical drain tube 111.

Additionally shown in FIGS. 11e and 11f, an inner septum 1114 includes a slit 1130 therein, generally along a central portion of its centerline. The slit 1130 enables a surgical drain tube 111 to be passed through inner septum 1114. The slit 1130 through inner septum 1114 functions to seal against air and liquid flow escaping from the fluid flow chamber 143 in the absence of surgical drain tube 111.

Figure 11G:
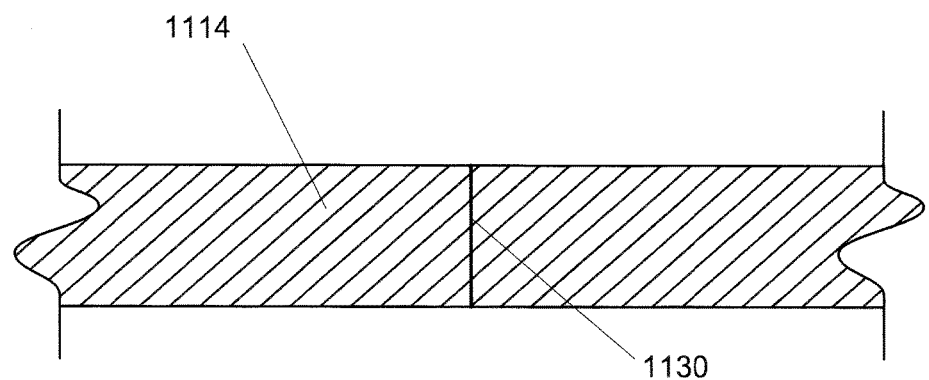
FIGS. 11g and 11h are partial sectional views of the alternative inner septum embodiment of FIGS. 11e and 11f, shown respectively with a closed slit in the absence of a drain tube and a slit penetrated by a drain tube.
Figure 11H:
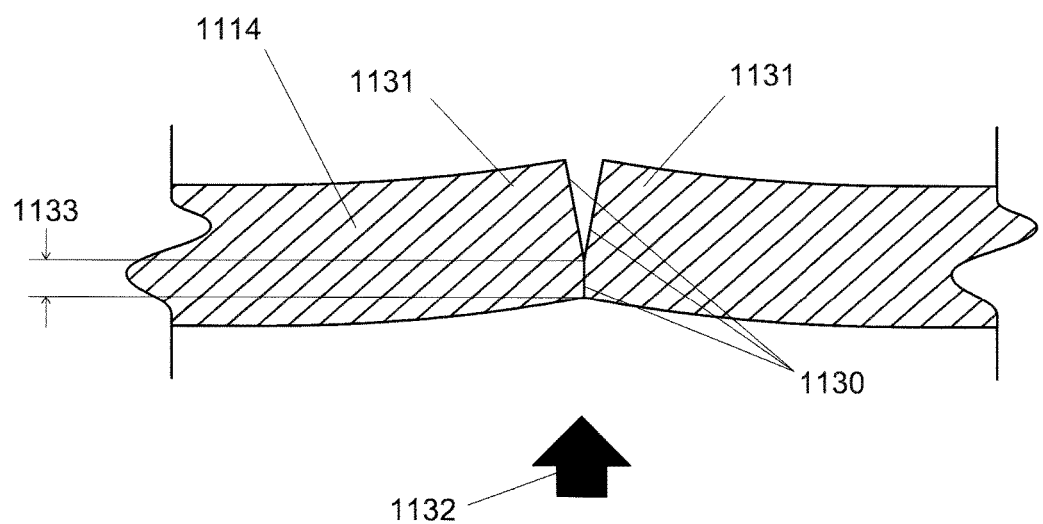

FIG. 11g is a cross sectional view of the inner septum 1114 of FIG. 11e, shown with the slit 1130 sealably closed in its static state. The inner septum should preferably be about 3-4 mm thickness of elastomeric material so that it is thick enough to prevent air or fluid pressure from forcing it to unseal in the absence of a drain tube 111. FIG. 11h is a cross sectional view of the inner septum showing the opposing sides 1131 of slit 1130 as they may flex to resist outward pressure 1132, for example should force be applied upon flexible fluid collection chamber 169 and transmitted through fluid flow chamber 143. Outward pressure 1132 upon the inner septum 1114 will create an interference fit 1133 between the opposing sides 1131 of the slit 1130, thereby sealing against escaping air or fluid. Whereas a slit 1130 achieves an effective seal through the inner septum 1114 in the absence of a drain tube 111, fluids and air may pass through voids 1134 (FIG. 11) at either end of the slit 1130 in the presence of an inserted drain tube 111. Therefore, the outer septum 1112 provides sealed closure when in use with an inserted surgical drain tube 111.

While the invention has been described in connection with a plurality of different aspects, as illustrated in the various figures and discussed herein, those of ordinary skill in the art will appreciate that other similar aspects or features may be used and modifications and additions may be made without deviating from the scope of the invention. For example, various features may have been described in particular detail with respect to one aspect of the invention, but such features may be incorporated into other aspects described herein without deviating from the scope of the invention contemplated by the disclosure. Accordingly, the invention is not to be limited by what has been particularly shown and described.

What is claimed is:

1. A fluid collection system comprising:
a baseplate having an adhesive backing configured to couple the baseplate to a patient's skin and defining a wafer having an approximately centrally positioned opening, and a ring shaped, radially-extending wafer connector coupled to said wafer and disposed around said opening configured to receive a first end of a surgical drain tube; and an appliance including a leaked fluid remover, said leaked fluid remover having a fluid remover connector operable to detachably couple with the wafer connector, the leaked fluid remover connector including a first housing element and a second housing element received by said first housing element and a spacer having an upper surface and a lower surface, the first housing element including an outer septum having a lower surface positioned on or coupled to the upper surface of the spacer, and the second housing element including an inner septum positioned on or coupled to the lower surface of the spacer; and a leaked fluid collector having an outer film and an inner film, the outer film coupled to an upper portion of the first housing component and the inner film coupled to a lower portion of the first housing component thereby coupling an interior of the leaked fluid collector to the fluid remover connector, wherein coupling of the fluid remover connector to the wafer connector forms a fluid flow chamber therebetween through which leaked fluid from the incision flows through the fluid flow chamber and into the leaked fluid collector.

2. The fluid collection system of claim 1 wherein said outer septum includes an orifice for receiving a surgical drain tube from a front side of the septum or a backside of the septum, said septum radially, axially and/or pivotally moveable within the septum space volume to alleviate side load tension on the septum as the surgical drain tube is displaced.

3. The fluid collection system of claim 1 wherein said leaked fluid remover connector is detachably coupled to the baseplate in a snap-fit arrangement.

4. The fluid collection system of claim 1 wherein said first housing element limits radial, axial and/or pivotal movements of the outer septum.

5. The fluid collection system of claim 4 wherein the leaked fluid collector is operably coupled to the leaked fluid collector along a periphery of the leaked fluid remover.

6. The fluid collection system of claim 5 wherein a fluid flow path of leaked fluids extends from a surgical incision through the wafer opening through the leaked fluid remover to a fluid flow chamber in said leaked fluid remover and out to the leaked fluid collector.

7. The fluid collection system of claim 1 wherein said spacer is configured to space apart the inner and outer septums to enable septum lips to splay up and down as a surgical drain tube is inserted from one direction or the other.

8. The fluid collection system of claim 1 wherein said outer septum includes a generally centered opening.

9. The fluid collection system of claim 8 wherein said generally centered opening is punches, molded or cut through the outer septum.

10. The fluid collection system of claim 8 wherein said generally centered opening is circular and compliant and configured to provide a fluid tight seal upon the fluid flow chamber when the fluid collection system is coupled to a surgical drain tube.

11. The fluid collection system of claim 1 wherein said inner septum includes a slit positioned along a central portion of a centerline thereof.

12. The fluid collection system of claim 11 wherein said slit is configured to enable a surgical drain tube to be passed through said inner septum.

13. The fluid collection system of claim 11 wherein said slit is configured to seal against air and liquid flow escaping from the fluid flow chamber in the absence of a surgical drain tube.

14. The fluid collection system of claim 1 wherein said inner septum comprises an elastomeric material of from 3 to 4 mm in thickness.

15. The fluid collection system of claim 11 wherein opposing sides of said slit flex to resist outward pressure.

16. The fluid collection system of claim 15 wherein said outward pressure upon the inner septum creates an interference fit between the opposing sides of said slit.

17. The fluid collection system of claim 1 wherein said outer septum is configured to provide a sealed closure against leaking fluids from the inner septum when a surgical drain tube in inserted therewithin.

* * * * *